United States Patent [19]

Legeais

[11] Patent Number: 5,713,956
[45] Date of Patent: Feb. 3, 1998

[54] MICROPOROUS SUPPORT FOR A KERATOPROSTHESIS

[75] Inventor: Jean-Marc Legeais, Saint-Mande, France

[73] Assignee: F.C.I. (France Chirurgie Instrumentation), France

[21] Appl. No.: 956,878
[22] PCT Filed: Feb. 19, 1992
[86] PCT No.: PCT/FR92/00159
  § 371 Date: Dec. 10, 1992
  § 102(e) Date: Dec. 10, 1992
[87] PCT Pub. No.: WO92/18065
  PCT Pub. Date: Oct. 29, 1992

[30] Foreign Application Priority Data

Apr. 10, 1991 [FR] France ............................ 91 04333

[51] Int. Cl.⁶ ............................................ A61F 2/14
[52] U.S. Cl. ............................... 623/5; 623/6; 623/11
[58] Field of Search ........................ 623/5, 4, 6, 11

[56] References Cited

U.S. PATENT DOCUMENTS

| | | |
|---|---|---|
| 2,714,721 | 8/1955 | Stone, Jr. ............................................ 3/1 |
| 4,229,838 | 10/1980 | Mano ............................................ 623/12 |
| 4,332,035 | 6/1982 | Mano ............................................ 623/12 |
| 4,373,519 | 2/1983 | Errede et al. ............................... 623/5 X |
| 4,687,482 | 8/1987 | Hanson ...................................... 623/12 X |
| 4,693,715 | 9/1987 | Abel, Jr. ............................................ 623/5 |
| 4,799,931 | 1/1989 | Lindstrom ..................................... 623/5 |
| 4,810,082 | 3/1989 | Abel, Jr. ........................................ 623/5 X |
| 4,863,974 | 9/1989 | Mallouk et al. ........................... 623/16 X |
| 4,865,601 | 9/1989 | Caldwell ..................................... 623/6 X |
| 4,923,466 | 5/1990 | Pintucci ......................................... 623/5 |
| 5,019,097 | 5/1991 | Knight et al. ................................. 623/5 |
| 5,077,215 | 12/1991 | McAuslan et al. ....................... 623/12 X |
| 5,300,115 | 4/1994 | Py ............................................... 623/5 X |

*Primary Examiner*—David Isabella
*Attorney, Agent, or Firm*—Eckert Seamans Cherin & Mellott

[57] ABSTRACT

A keratoprosthesis support made of EPTFE provides the connection between the corneal prosthesis and the eyeball. The thickness of the expanded polytetrafluoroethylene is about 0.2 mm, and its channels having a diameter of about 50 microns are mutually parallel and perpendicular to the surface. Applications: obtaining supports that are transparent and hydrophilic.

3 Claims, No Drawings

MICROPOROUS SUPPORT FOR A KERATOPROSTHESIS

The present invention relates to a support for mesoprothesis, i.e. a prosthesis having one portion outside the organism and a second portion inside it. It relates particularly, but not exclusively, to corneal prostheses or a "keratoprostheses".

Keratoprostheses remain the ultimate recourse for bilateral corneal blindness when homografts are not effective. However, given the tendency of the organism to reject or to include any foreign body, installing such prostheses gives rise to numerous complications, and in particular: ocular hypertension; retinal detachment; conjunctive necroses; scleral ulceration; and prosthesis expulsion, which presently happens at a rate of about 50% after five years.

These complications arise essentially from the connection between the eyeball and the prosthesis. In order to improve the quality of this connection or "haptic", proposals have already been made to use a porous support that can be colonized by cells so that cellular tissue is reconstituted in the connection zone. The use of expanded polytetrafluoroethylene (EPTFE) is described in the journal "Francais d'Ophtalmologie", (1987, 10, 6/7, pp. 425–433) under the title (in translation) "Study of an expanded polytetrafluoroethylene support" by Mr. Legeais and Mr. Renard.

Other colonizable chemical compounds have also been proposed in FR-A-2 608 041.

In the technique that is currently performed, a patch having a diameter of about 10 mm is cut out from a 0.4 mm thick sheet of EPTFE, and the center of the patch is pierced to receive the lens. The mean diameter of the pores is 20 microns and it is observed that the pores are colonized by cells. However the EPTFE remains opaque, i.e. white, and the connection remains hydrophobic.

An object of the present invention is to mitigate this drawback, to enable the haptic to be completely colonized, and to make the colonized structure hydrophilic.

According to the present invention, the EPTFE support for a keratoprosthesis is characterized in that the pores or channels thereof are parallel and oriented perpendicularly to the surface of the support.

According to another characteristic of the invention, the thickness of the support is substantially equal to 0.2 mm. The observed phenomenon of transparency disappears from the colonized product as from a thickness of about 0.3 mm.

Finally, the diameter of the pores or the channels lies in the range 20 microns to 150 microns, and is about 50 microns, for example.

Under such conditions, histological sections show good colonization and the presence of fibroblasts and of proteins inside the channels.

Surprisingly, the support begins to become translucent after being implanted for ten days and becomes completely transparent around the 20th to 25th day, thus providing a considerable advantage from the point of view of appearance.

In addition, after colonization, the support which is physically hydrophobic becomes, hydrophilic, thereby enabling it to be irrigated. It behaves as though the support per se has acquired new physicochemical properties, namely both hydrophily and a change of refractive index, thus creating an artificial hybrid organ.

Naturally numerous variants can be applied, in particular by substituting technically equivalent means, without thereby going beyond the ambit of the invention.

I claim:

1. A mesoprosthesis support for a mesoprosthesis, the mesoprosthesis support comprising at least a layer of expanded polytetrafluoroethylene having channels parallel to one another, the channels being perpendicular to a surface of the support.

2. A mesoprosthesis support according to claim 1, wherein the support thickness is substantially equal to 0.2 mm.

3. A mesoprosthesis support according to claim 1 or 2, wherein the mean diameter of the channels lies in the range of 20 microns to 150 microns.

* * * * *